(12) United States Patent
Tryggvason et al.

(10) Patent No.: US 8,469,931 B2
(45) Date of Patent: Jun. 25, 2013

(54) MEDICAL PRODUCT, AND A METHOD OF HANDLING A MEDICAL SYSTEM

(75) Inventors: Ragnar Tryggvason, Löddeköpinge (SE); Peder Flank, Bjärred (SE)

(73) Assignee: Gambro Lundia AB, Lund (SE)

( * ) Notice: Subject to any disclaimer, the term of this patent is extended or adjusted under 35 U.S.C. 154(b) by 641 days.

(21) Appl. No.: 12/531,023

(22) PCT Filed: Mar. 4, 2008

(86) PCT No.: PCT/SE2008/050241
§ 371 (c)(1),
(2), (4) Date: Sep. 11, 2009

(87) PCT Pub. No.: WO2008/111900
PCT Pub. Date: Sep. 18, 2008

(65) Prior Publication Data
US 2010/0137840 A1      Jun. 3, 2010

Related U.S. Application Data

(60) Provisional application No. 60/894,309, filed on Mar. 12, 2007.

(30) Foreign Application Priority Data

Mar. 12, 2007 (SE) ...................................... 0700622

(51) Int. Cl.
*A61M 5/00* (2006.01)
(52) U.S. Cl.
USPC ...................................... 604/246; 604/167.05
(58) Field of Classification Search
USPC .............. 604/246, 248, 249, 167.05
See application file for complete search history.

(56) References Cited

U.S. PATENT DOCUMENTS

| 4,431,424 | A | 2/1984 | Svensson |
| 5,855,230 | A | 1/1999 | Guala et al. |
| 6,447,473 | B1 * | 9/2002 | Levine et al. ................... 604/33 |
| 2005/0016620 | A1 | 1/2005 | Proulx et al. |
| 2005/0150546 | A1 | 7/2005 | Liepold et al. |
| 2008/0114295 | A1 * | 5/2008 | Glynn ........................... 604/110 |

FOREIGN PATENT DOCUMENTS

| EP | 0 028 601 | 8/1983 |
| WO | WO-98/50105 | 11/1998 |
| WO | WO-03/086528 A1 | 10/2003 |
| WO | 2005/016443 A1 | 2/2005 |
| WO | WO-2005/117802 A1 | 12/2005 |

* cited by examiner

*Primary Examiner* — Kevin C Sirmons
*Assistant Examiner* — Deanna K Hall
(74) *Attorney, Agent, or Firm* — Nixon & Vanderhye P.C.

(57) ABSTRACT

A medical product configured for use in a medical system and a method of handling a medical system comprising a first subsystem and a second subsystem containing a medical fluid are provided. A connector connects the first and second subsystems for transport of the medical fluid from one of the subsystems to the other subsystem. The connector comprises a valve device, a first connection pipe connectable to the first subsystem, and a second connection pipe connectable to the second subsystem. The valve device comprises a first part and a second part, which are movable in relation to each other to permit an opening movement from a closed position, preventing a fluid communication between the first and second connection pipes, and an open position permitting the fluid communication. The medical product comprises a blocking member preventing, in a blocking state, the opening movement, and permitting changing of the blocking state to a non-blocking state permitting the opening movement.

37 Claims, 6 Drawing Sheets

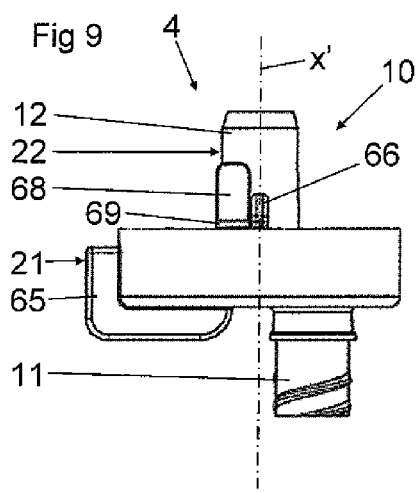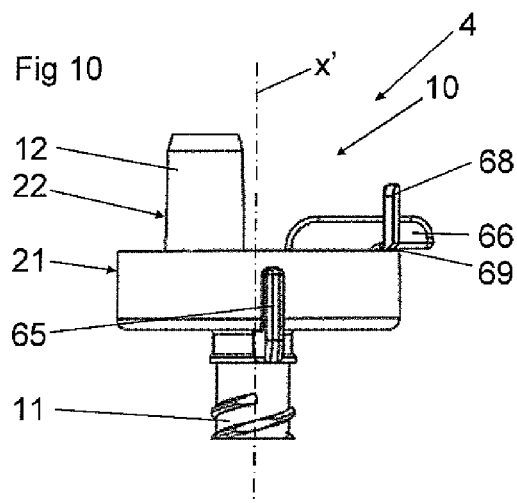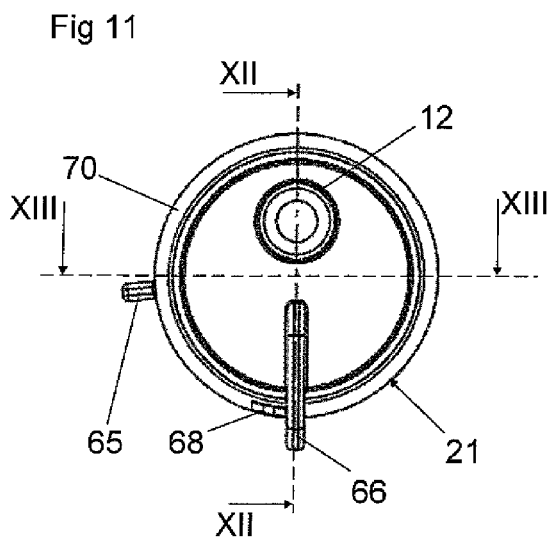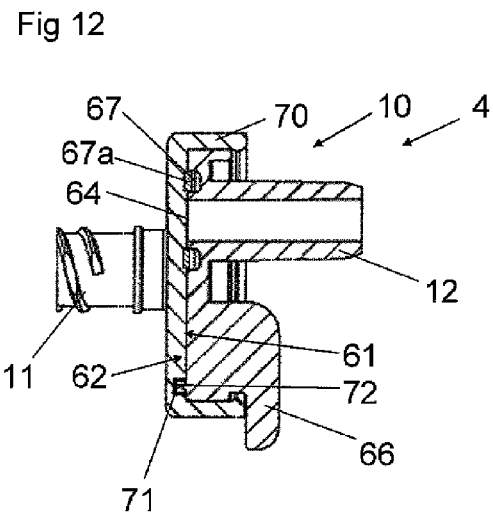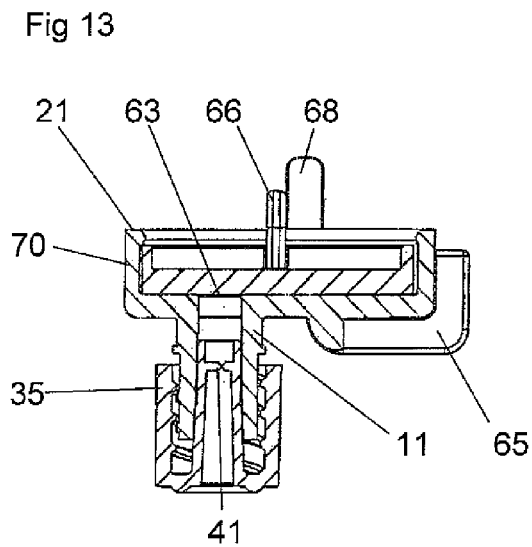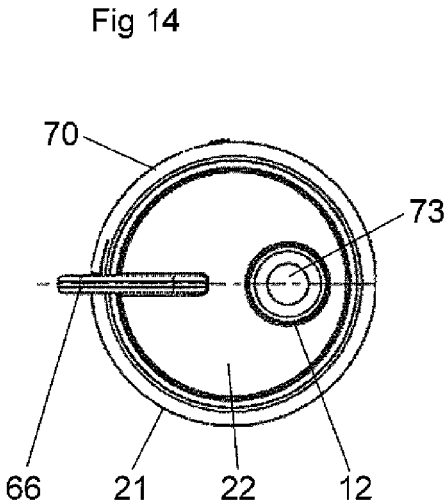

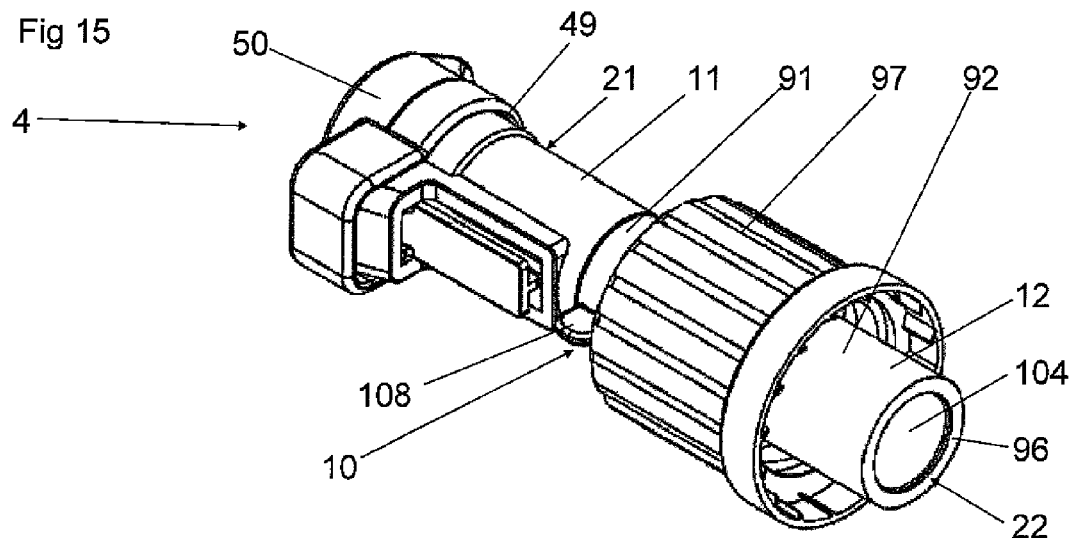
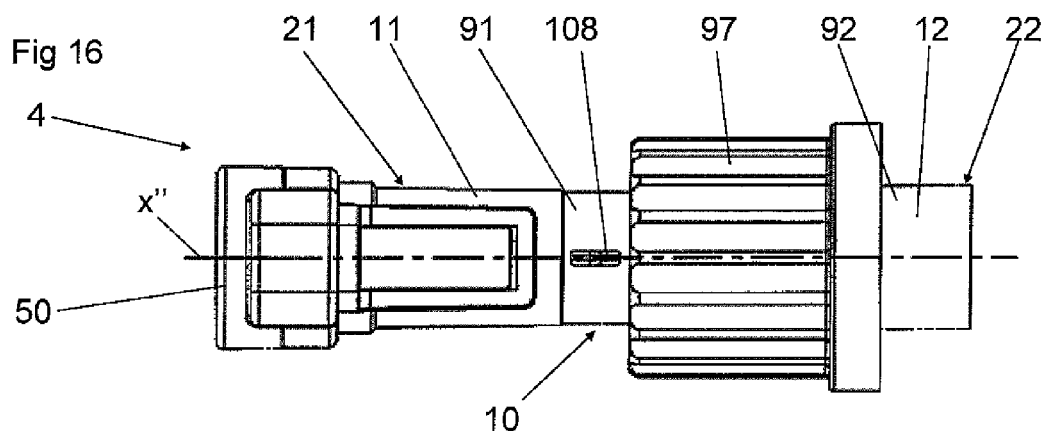
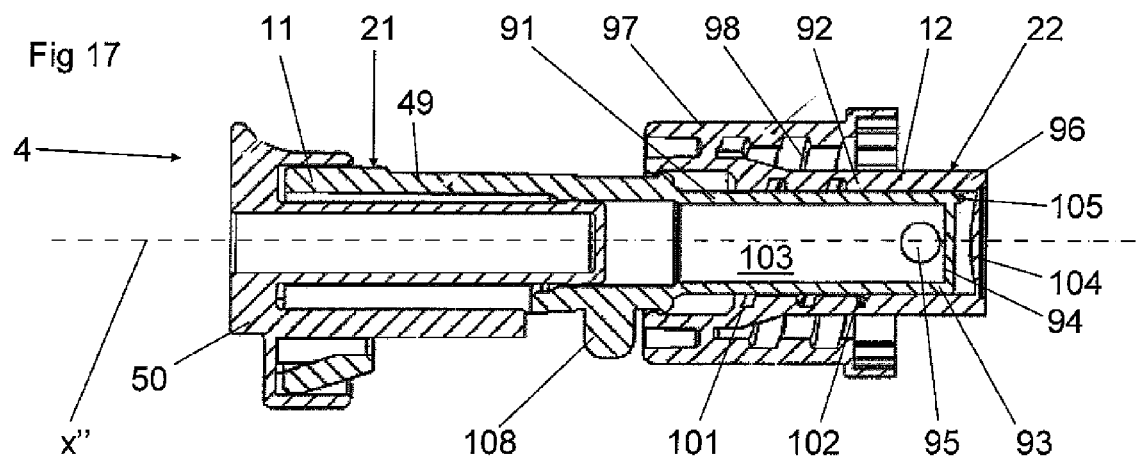

US 8,469,931 B2

MEDICAL PRODUCT, AND A METHOD OF HANDLING A MEDICAL SYSTEM

CROSS REFERENCE TO RELATED APPLICATION

This application is a National Phase application based on PCT/SE2008/050241 filed Mar. 4, 2008, which claims the priority of Swedish Patent Application No. 0700622-4, filed Mar. 12, 2007, and claims the benefit of U.S. Provisional Application No. 60/894,309, filed Mar. 12, 2007, the content of all of which is incorporated herein by reference.

THE TECHNICAL FIELD OF THE INVENTION

The present invention refers to a medical product and to a method of handling a medical system comprising a first subsystem and a second subsystem.

In the medical field, there are numerous situations where a medical fluid is to be transported from one subsystem to another subsystem during sterile conditions for preventing contamination of the medical fluid or any one of the subsystems. In a first possible application of the present invention, the first subsystem may be a system for supplying infusion liquid to the blood system of a patient. A second application of the present invention may include the transfer of blood products or the transfer of blood from the blood system of an individual to the blood system of another individual, either directly between the individual or via any system for storing blood. Further applications of the present invention may include any supply of other medical fluids into the body of an individual. A common aspect of these applications is that one of the subsystems is a biological system, such as the blood system of an individual. However, the present invention is also applicable to the transport of a medical fluid between two non-biological subsystems, for instance during the manufacture, cleaning, processing or treating of medical fluids.

In the following, the present invention will be described in connection with a further important application of the invention, namely dialysis. However, the invention is not restricted to this application, but may be applied to other fields as defined above.

There are various dialysis therapies used today. One differs between extracorporeal dialysis, such as hemodialysis and intensive care dialysis, and intracorporeal dialysis, such as peritoneal dialysis.

During a dialysis treatment, a medical fluid, i.e. a dialysis liquid, is used. The dialysis liquid may be contained in a container, which is connected directly to the patient in intracorporeal dialysis or to a dialysis apparatus in extracorporeal dialysis, via a so-called connector. Typically, the connector is connected to the container, directly or indirectly via a line. The container may be manufactured in a flexible material, preferably a plastic material. Before use the connector is closed by means of a frangible pin arranged in the flow passage of the connector and preventing a flow of the medical fluid from the container through the connector. Such a container including a frangible pin is disclosed in WO 2005/117802. When the medical fluid is to be used, the connector is connected to the patient or the dialysis apparatus via a line. The frangible pin is then removed by being broken off. A disadvantage of this known connector design is that the connector does not permit closing of the fluid communication once the connector has been opened, e.g. if medical fluid remains after the dialysis treatment has been finished or if the dialysis treatment is interrupted in advance for any reason. Another disadvantage is that the breaking of the frangible pin could be experienced as difficult for certain users, e.g. patients with a poor health condition.

EP-B-28601 shows a slide valve and a coupler assembly for medical applications, such as peritoneal dialysis applications and collection of urine. The slide valve comprises a valve housing forming a fluid passage. A cylinder with a piston is arranged transversally to the fluid passage. The piston is movable in the cylinder between a closed position and an open position. Some provisions are made for sterilizing the slide valve.

U.S. Pat. No. 4,431,424 discloses a slide valve for medical applications. A disinfectant is supplied to the interior of the valve before the valve is connected to a coupling element.

SUMMARY OF THE INVENTION

The object of the present invention is to remedy the disadvantages mentioned above. A further object of the present invention is to provide a technical solution for a simple and reliable connector in a medical system. A further object is to provide a technical solution, which avoids the frangible pin. A further object is to provide a medical product making use of few components.

This object is achieved by the medical product initially defined, which is characterized in that it comprises a blocking member configured, in a blocking state, to prevent the opening movement from the closed stable position to the open stable position, and further configured to permit changing of the blocking state of the blocking member to a non-blocking state permitting the opening movement from the closed stable position to the open stable position. By means of such a valve device, the frangible pin contained in the medical fluid or flow passage is avoided, and at the same time the user may easily establish whether the medical product has been used or not by observing the state of the blocking member. If the blocking member is in the blocking state, the user can be sure that a new fresh medical fluid is provided.

According to an embodiment of the invention, the blocking member is provided on the valve device. It is advantageous to have the blocking member in the proximity of the valve device to be operated by the user.

According to a further embodiment of the invention, the blocking member is configured to permit the changing of the blocking state of the blocking member to the non-blocking state by a user applying a determined force to the blocking member. Such a change of state is easy to perform by a user, who might be in a weak condition due to the disease. Advantageously, the blocking member is configured to permit the application of the force directly to the blocking member itself. The blocking member may also, possibly as an alternative or a complement, be configured to permit the application of the force to at least one of the first part and the second part for changing the state of the blocking member. Furthermore, the blocking member may be configured in such way that the changing of the blocking state of the blocking member to the non-blocking state is performed by removing the blocking member.

According to a further embodiment of the invention, the first part and the second part are configured to remain in the open stable position when the open stable position has been obtained. Furthermore, the first part and the second part may, in the non-blocking state of the blocking member, be movable by a user applying a determined force in order to permit a closing movement from the open stable position to the closed stable position.

According to a further embodiment of the invention, the medical product comprises a cover element attachable to the first connection pipe for protecting the interior of the first connection pipe, wherein the cover element is removable before the first connection pipe is connected to the first connection portion of the first subsystem.

According to a further embodiment of the invention, the second subsystem comprises a container containing the medical fluid, wherein the container is comprised by the medical product and connected to the second connection pipe of the connector.

According to a further embodiment of the invention, the blocking member is configured to permit changing of the blocking state to the non-blocking state in an irreversible manner by means of a breakable attachment. In such a way, it is not possible to hide the fact that the state of the blocking member has been changed, which means the at least a part of the medical fluid might have been used or tampered with.

According to further embodiment of the invention, the first part comprises a housing, through which the channel extends and which comprises a cylinder forming an inner chamber extending transversally to and crossing the channel, wherein the second part comprises a piston, which is movable in the inner chamber between the closed stable position closing the channel and the open stable position, in which the channel is open by means of a recess in the piston. Such a valve device can be handled in a convenient manner by a user, such as a patient, by moving the piston of the second part after the changing of the state of the blocking member.

According to a further embodiment of the invention, the blocking member is provided on one of the piston and the cylinder. Advantageously, the cylinder has a primary end and a secondary end, and the piston has a primary end and a secondary end, wherein the primary end of the piston protrudes from the primary end of the cylinder in the closed stable position and wherein the secondary end of the piston protrudes from the secondary end of the cylinder in the open stable position.

According to a further embodiment of the invention, the blocking member is provided on the piston at the primary end of the piston. Advantageously, the blocking member may be configured as a part of a removable ring extending around the piston at the primary end. Such a ring may be manufactured and provided on the piston in an easy manner to prevent any movement of the piston in relation to the cylinder. Although the above-mentioned solution is advantageous, it is also possible to provide the blocking member on the cylinder.

According to a further embodiment of the invention, the piston has a primary end portion, which is provided at the primary end of the piston and which is configured to prevent the primary end of the piston from entering the inner chamber of the cylinder, and a secondary end portion, which is provided at the secondary end of the piston and which is configured to prevent the secondary end of the piston from entering the inner chamber of the cylinder. The removable ring may then be provided between the primary end of the cylinder and the primary end portion of the piston. Advantageously, the blocking member may be attached to the piston via breakable attachment.

According to a further embodiment of the invention, the piston is manufactured in a piston material and the cylinder in a cylinder material, wherein the piston material is softer than the cylinder material. Such a relatively soft material will function as sealing means having a sealing effect and thus contribute to a tight abutment between the inner wall of the cylinder and the outer surface of the piston. In such a way leakage of the medical fluid is prevented. In addition, the piston may be provided with further sealing means in order to provide a tight sealing against an inner wall of the cylinder. Such further sealing means may then comprise at least one ridge extending outwardly from an outer surface of the piston and around an outer periphery of the piston. Such a ridge, for instance of the above-mentioned relatively soft material, will ensure a tight abutment against the inner wall of the cylinder.

According to another embodiment of the invention, the first part comprises a first abutment surface through which the first connection pipe extends via a first aperture, and the second part comprises a second abutment surface through which the second connection pipe extends via a second aperture, wherein the first and second abutment surfaces are facing each other and rotatable in relation to each other around a common axis of rotation, wherein the first aperture and the second aperture are eccentric with respect to the axis of rotation. Also such a valve device may be handled in an easy manner by a user, such as a patient, by simply rotating the first and second part relatively to each other.

According to a further embodiment of the invention, one of the first part and the second part comprises a projecting member and the blocking member is attached to the other of the first and second parts in order to cooperate with the projecting member in such a way that the opening movement is prevented as long as the blocking member is in the blocking state.

According to a further embodiment of the invention, the first part comprises a first projecting member and the second part a second projecting member, wherein the first and second projecting members are aligned in the open stable position and at an angle distance from each other with respect to the axis of rotation in the closed stable position. The projecting members, in addition to serve as gripping members for operation of the valve device, may also serve as a clear indicator as to whether the valve device is in the open stable position or the closed stable position.

According to a further embodiment of the invention, one of the first part and the second part has a circumferential flange extending around the first abutment surface or the second abutment surface, thus forming a receiving cavity for the other of the first part and the second part.

According to a further embodiment of the invention, at least one of the first part and the second part comprises sealing means extending through the first abutment surface or the second abutment surface around the first aperture or the second aperture. Advantageously, the sealing means comprises a groove and a seal element provided in the groove.

According to another embodiment of the invention, the valve device comprises a membrane closing the channel in the closed stable position, and breaking means configured to break the membrane during the opening movement in order to open the channel. With such a configuration, a further security is achieved, i.e. in addition to change the state of the blocking member, also the membrane has to be broken before the channel and the fluid communication can be established.

According to another embodiment of the invention, the first part comprises a first pipe, which has an outer end portion forming the first connection pipe and an inner end portion having a closed end but at least one lateral opening, and the second part comprises a second pipe, which forms the second connection pipe and is configured to receive the first pipe, wherein the first pipe is movable along a longitudinal axis in the second pipe to permit the opening movement between the closed stable position, in which the lateral opening is located opposite to an inner wall of the second pipe, and the open stable position, in which the inner end portion and the lateral opening of the first pipe protrude from outer end portion of the second pipe. Also such a valve device may be handled in an easy manner by a user, such as a patient, by simply moving the first part, i.e. the first pipe, and the second part, i.e. the second pipe relatively to each other.

According to a further embodiment of the invention, the membrane is provided at second pipe to cover the outer end portion, wherein the breaking means are formed by the inner end portion of the first pipe. Advantageously, the breaking means may comprise a protrusion protruding from the inner end portion of the first pipe.

According to a further embodiment of the invention, the first pipe and the second pipe are provided with at least one thread, wherein the opening movement along the longitudinal axis is obtained by rotating the first and second pipes relatively to each other.

According to a further embodiment of the invention, the blocking member is provided on the first pipe. Advantageously, the blocking member is attached to the first pipe via a breakable attachment. Furthermore, the blocking member may be configured as a part of a removable ring extending around the first pipe.

The object is also achieved by the method initially defined, wherein the first subsystem has a first connection portion and the second subsystem has a second connection portion, at least one of the subsystems containing a medical fluid, and wherein a connector connects the first and second subsystems to each other and comprises a valve device comprising a first part and a second part; a first connection pipe connected to the valve device and configured to be connected to the first connection portion of the first subsystem; and a second connection pipe connected to the valve device and configured to be connected to the second connection portion of the second subsystem, the method comprising the steps of:

changing a blocking state of a blocking member, preventing an opening movement of the first part and the second part in relation to each other, to a non-blocking state, moving the first part and the second part in relation to each other from a closed stable position, preventing fluid communication between the first connection pipe and the second connection pipe, and an open stable position, forming a channel permitting fluid communication between the first connection pipe and the second connection pipe, and transporting the medical fluid from one of the subsystems to the other subsystem.

BRIEF DESCRIPTION OF THE DRAWINGS

The present invention is now to be explained more closely by the description, by way of example only, of various embodiments and with reference to the drawings attached hereto.

FIG. 9 discloses a side view of a connector of a medical product according to a third embodiment of the invention.

FIG. 10 discloses another side view of the connector in FIG. 9.

FIG. 11 discloses a top view of the connector in FIG. 9 in a closed stable position.

FIG. 12 discloses a sectional view along the line XII-XII in FIG. 11.

FIG. 13 discloses a sectional view through a first part of the connector along the line XIII-XIII in FIG. 11.

FIG. 14 discloses a top view of the connector in FIG. 9 in an open stable position.

FIG. 15 discloses a perspective view of a connector of a medical product according to a fourth embodiment of the invention.

FIG. 16 discloses a side view of the connector in FIG. 15.

FIG. 17 discloses a sectional view along the lines XVII-XVII in FIG. 16.

DETAILED DESCRIPTION OF VARIOUS EMBODIMENTS

Figure 1:
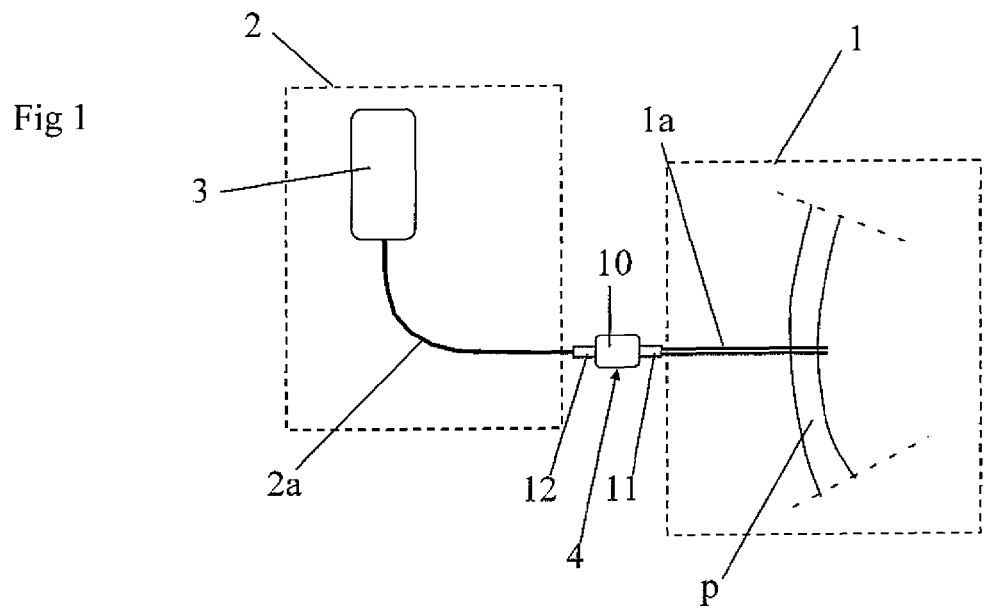
FIG. 1 discloses schematically an example of a first medical system.

FIG. 1 discloses a medical system which illustrates schematically intracorporeal dialysis care, such as peritoneal dialysis, and comprises a first subsystem 1 having a first connection portion 1a and a second subsystem 2 having a second connection portion 2a. In FIG. 1, the first subsystem 1 comprises a patient p, whereas the second subsystem 2 comprises a container 3 with a medical fluid in the form of a dialysis liquid. The first connection portion 1a of the first subsystem 1 is connected to the second connection portion 2a of the second subsystem 2 via a connector 4 in order to permit transport of the medical fluid from the second subsystem 2, in this example the container 3, to the first subsystem 1, in this example the patient p. The first connection portion 1a comprises a flexible line with an appropriate connection member adapted to be connected to the connector 4. The second connection portion 2a also comprises a flexible line with an appropriate connection member adapted to be connected to the connector 4. A medical product is constituted by the connector 4 and the second subsystem 2. A medical product may also be constituted by the connector 4 only.

Figure 2:
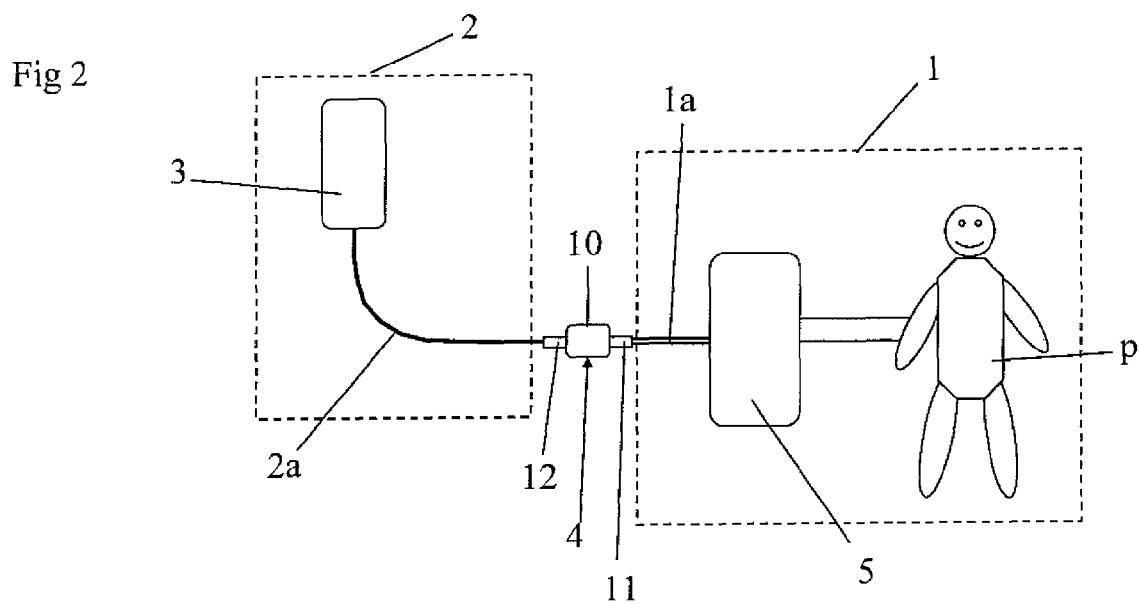
FIG. 2 discloses schematically an example of a second medical system.

FIG. 2 discloses another medical subsystem, which illustrates schematically extracorporeal dialysis, such as hemodialysis care or acute renal care dialysis, and differs from the first medical system in that the first system 1 comprises a dialysis apparatus 5 to which a patient p is connected, and that the blood is treated extracorporeally.

The connector 4 will be described more closely below in conjunction with the description of the various embodiments. Generally, the connector 4 comprises a valve device 10, a first connection pipe 11 and a second connection pipe 12. The first connection pipe 11 is connected to the valve device 10 and configured to be connected to the first connection portion 1a of the first subsystem, in the example disclosed to the line and the connection member of the first connection portion 1a. The second connection pipe 12 is connected to the valve device 10 and is, or configured to be, connected directly to the container 3 or indirectly to the container 3 via the second connection portion 2a of the second subsystem 2, in the example disclosed to the line and the connection member of the second connection portion 2a.

Figure 3:
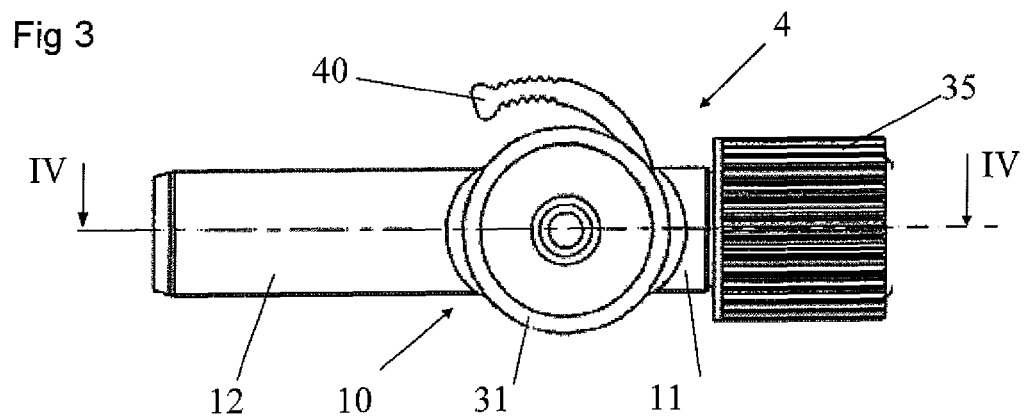
FIG. 3 discloses a side view of a connector of a medical product according to a first embodiment of the invention.
Figure 4:
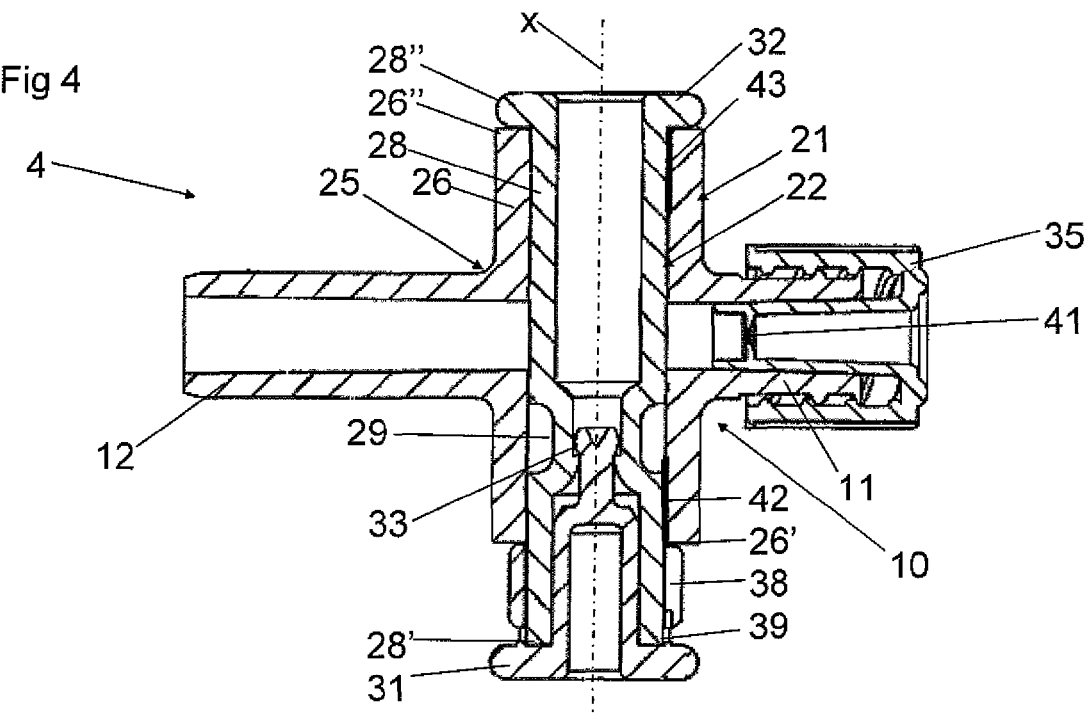
FIG. 4 discloses a sectional view along the line IV-IV in FIG. 3.
Figure 5:
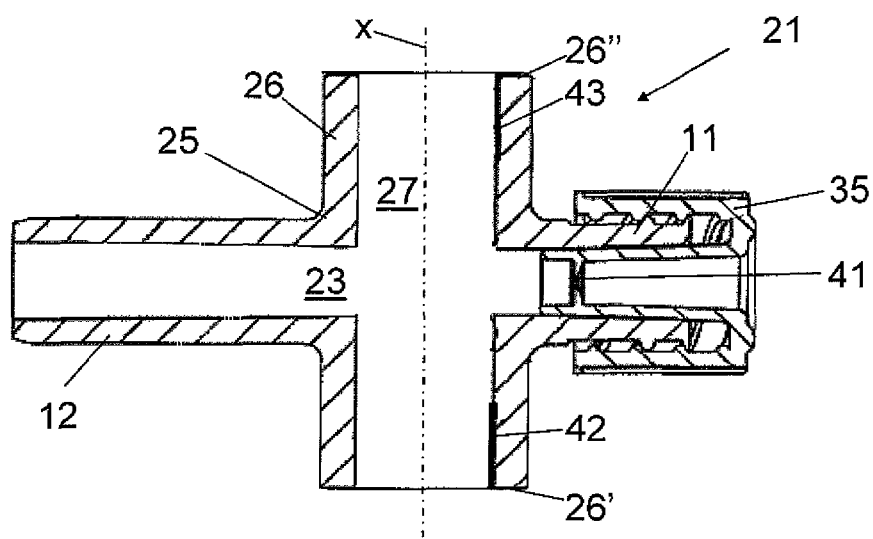
FIG. 5 discloses a sectional view of a first part of the connector in FIG. 4.

With reference to FIGS. 3 to 7, a first embodiment is to be described. FIGS. 3 and 4 discloses the connector 4 with the valve device 10, the first connection pipe 11 and the second connection pipe 12. The valve device 10 comprises a first part 21 and a second part 22. Described in a general manner, the first part 21 and the second part 22 are movable in relation to each other to permit an opening movement from a closed stable position, preventing fluid communication with the first connection pipe 11 and the second connection pipe 12, see FIG. 4, and an open stable position, forming a channel 23 permitting fluid communication between the first connection pipe 11 and the second connection pipe 12.

More specifically, in the first embodiment the first part 21 and the second part 22 are movable in relation to each other along a longitudinal axis x. The first part 21 comprises a housing 25 through which the channel 23 extends, see FIG. 5. The housing 25 comprises a cylinder 26 forming an inner chamber 27 which extends along the longitudinal axis x transversally to and crossing the channel 23. The second part 22 comprises a piston 28, which is movable in the inner chamber 27 of the cylinder 26 between the closed stable position closing the channel 23 and the open stable position, in which the channel 23 is open by means of a recess 29 in the piston 28, see also FIGS. 6 and 7. In the first embodiment disclosed, the recess 29 is formed by a groove extending around the periphery of the outer surface of the piston 28. The recess 29 may however also have a different shape, for instance as a cavity or a hole extending through the piston 28.

The cylinder 26 has a primary end 26' and a secondary end 26". The piston 28 has a primary end 28' and a secondary end 28". In the closed stable position shown in FIG. 4, the primary end 28' of the piston 28 protrudes from the primary end 26' of the cylinder 26. In the open stable position, the secondary end 28" of the piston 28 protrudes from the secondary end 26" of the cylinder 26.

Furthermore, the piston 28 has a primary end portion 31, which is provided at the primary end 28' of the piston 28. The primary end portion 31 comprises a flange preventing the primary end 28' from entering the inner chamber 27 of the cylinder 26. The piston 28 also has a secondary end portion 32, which is provided at the secondary end 28" of the piston 28. The secondary end portion 32 comprises a flange preventing the secondary end 28" of the piston 28 from entering the inner chamber 27 of the cylinder 26.

Figure 6:
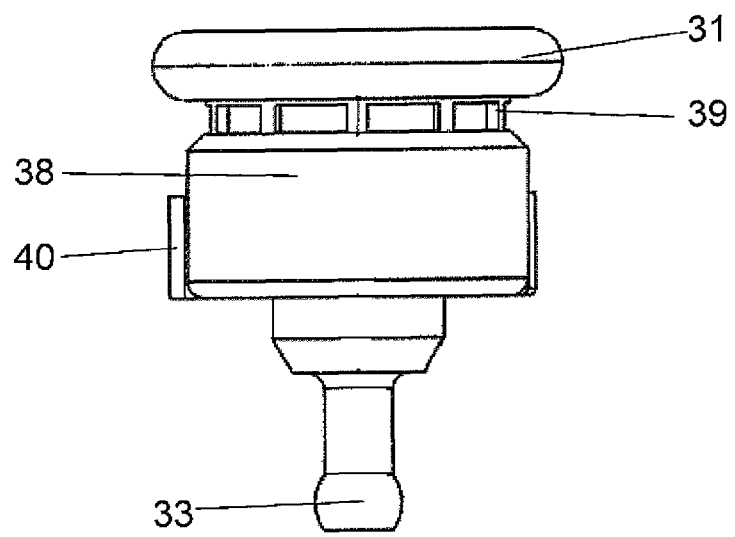
FIG. 6 discloses a side view of an end portion of a second part of the connector in FIG. 3.
Figure 7:
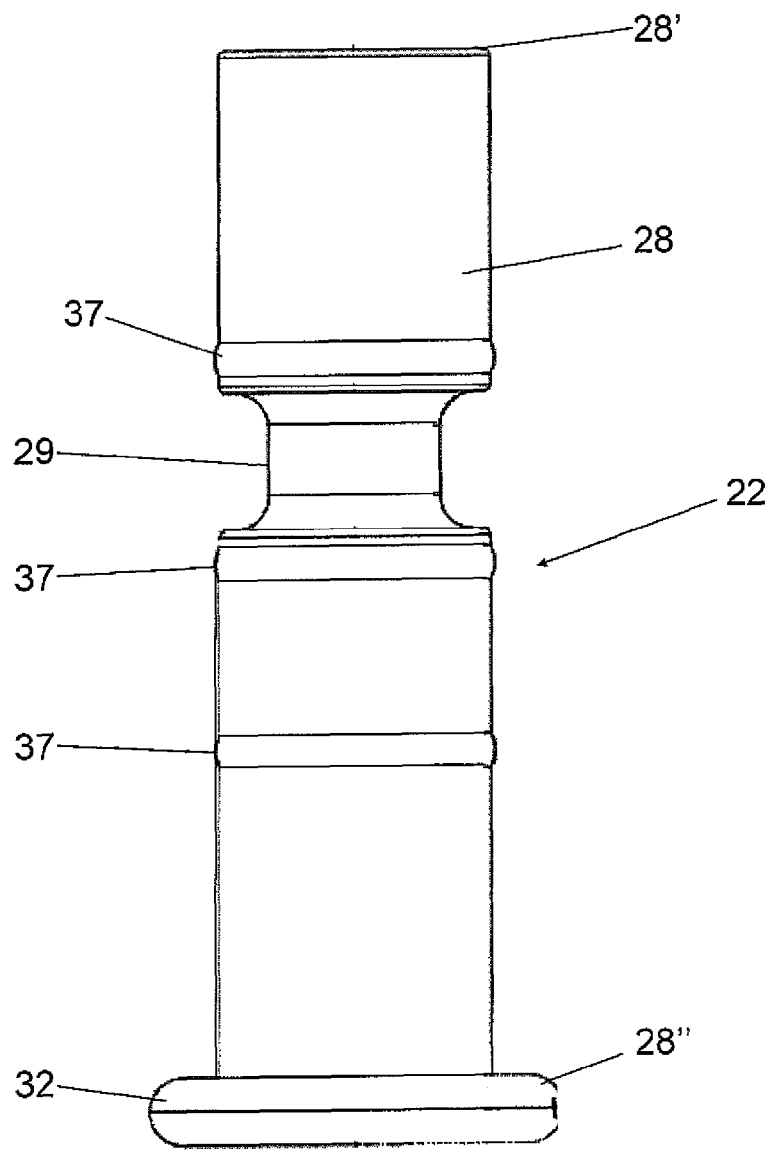
FIG. 7 discloses a side view of a piston of a second part of the connector in FIG. 3.

As can be seen from FIG. 4, the primary end portion 31 is formed by a separate part which is introduced into an inner space of the piston 28 and attached to the piston 28 in the inner space by means of a hook connection 33, see also FIGS. 6 and 7. In FIGS. 6 and 7, the two parts are separated from each other, i.e. before mounting of the valve device 10.

The piston 28, at least the part comprising the secondary end portion 32, is manufactured in a piston material and the cylinder 26 in a cylinder material. The piston material is softer than the cylinder material in order to improve the sealing between the outer surface of the piston 28 and the inner wall of the cylinder 26. As can be seen from especially FIGS. 6 and 7, the piston 28 is provided with further sealing means in order to provide a tight sealing against an inner wall of the cylinder 26. This further sealing means comprises three ridges 37 extending outwardly from the outer surface of the piston 28 and around an outer periphery of the piston 28. In the first embodiment disclosed, two of the ridges 37 are provided between the recess 29 and the secondary end 28" of the piston 28, and one ridge 37 is provided between the recess 29 and the primary end 28' of the piston 28.

As can be seen in FIGS. 3 and 4, the connector 4 also comprises a cover element 35, which is attached to the first connection pipe 11 for protecting the interior of the first connection pipe 11. The cover element 35 is attached to the first connection pipe 11 in a removable manner by means of a thread on the outer surface of the first connection pipe 11 and a corresponding thread on the inner surface of the cover element 35. The cover element 35 is removed from the first connection pipe 11 by being unscrewed before the first connection pipe 11 is connected to the first connection portion 1a of the first subsystem 1.

The connector 4 also comprises a blocking member 38. The blocking member 38 is, in a blocking state, configured to prevent the opening movement from the closed stable position to the open stable position. Furthermore, the blocking member 38 is configured to permit changing of the blocking state of the blocking member 38 to a non-blocking state permitting the opening movement from the closed stable position to the open stable position. The blocking member 38 is provided on the valve device 10, and in the first embodiment on the piston 28 at the primary end 28' of the piston 28. More specifically, the blocking member 38 is provided between the primary end 26' of the cylinder 26 and the primary end portion 31 of the piston 28. In the first embodiment, the blocking member 38 is configured as a removable ring extending around a main part of the periphery of the piston 28 at the primary end 28'. The blocking member 38, e.g. the ring, is attached to the piston 28 via a breakable attachment 39. The breakable attachment 39 may be obtained by one or several thin, weakened connecting strips.

The blocking member 38 is thus configured to permit the changing of the blocking state of the blocking member 38 to the non-blocking state by a user applying a determined force to the blocking member 38. In the first embodiment, this force is applied, as a pulling force, to a flap 40 of the blocking member 38 protruding outwardly from the blocking member 38. The user thus pulls the flap 40 whereby the pulling force applied will break the breakable attachment 39 in an irreversible manner and remove the blocking member 38 from the piston 28. After this changing of the blocking state of the blocking member 38, the piston 28 may then be moved along the longitudinal axis x from the closed stable position, disclosed in FIG. 4, to an open position in which the recess 29 establishes the channel 23 permitting fluid communication from the second connection pipe 12 to the first connection pipe 11, or possible vice versa.

It is to be noted here, that the first part 21, comprising the cylinder 26, and the second part 22, comprising the piston 28, are configured to remain in the open stable position when the open stable position has been obtained, i.e. after the opening movement along the longitudinal axis x. However, it is also to be noted that the first part 21, comprising the cylinder 26, and the second part 22, comprising the piston 28, in the non-blocking state of the blocking member 38, are moveable by a user applying a determined force in order to permit a closing movement from the open stable position back to the closed stable position disclosed in FIG. 4. After this closing movement, the removed blocking member 38 will serve as an indication to the user or any other person involved, that the connector 4 or the medical product may once have been used. For instance, a part of the medical fluid contained in the container 3 may have been used and the remaining part of the medical fluid may then be intended for waste or for use at a later occasion, preferably within a prescribed time limit. Even if the blocking member 38, e.g. in the form of a ring, for any reason is reattached onto the piston 28, the user may still observe that the medical product has been used thanks to the broken breakable attachment 39.

The connector 4 also comprises a number of small passages 41, 42, 43 permitting, in the closed stable position, an introduction of a sterilizing gas in such a way that the sterilizing gas will contact wall surfaces defining the channel 23. These small passages 41, 42, 43 thus enable sterilization of the connector 4 before use, i.e. before the blocking state of the blocking member 38 has been changed. Especially, it is to be noted that the connector 4 could be sterilized together with the container 3 and the second connection portion 2a, for instance during an autoclaving process. During the autoclaving process, sterilizing gas is thus permitted to enter the interior of the connector 4 through the small passages 41, 42, 43.

One such small passage 41 extends through the cover element 35 for enabling introduction of the sterilizing gas into the interior of the first connection pipe 11. Consequently, the inner wall surface of the first connection pipe 11 and a part of the outer surface of the piston 28 will thus be subjected to the sterilizing gas.

Two further small passages 42, 43 comprises a respective sterilizing groove formed in the inner wall surface of the cylinder 26 and extending from the primary end 26' of the cylinder 26 and the secondary end 26" of the cylinder 26, respectively. As can be seen in FIG. 4, the sterilizing groove of the small passage 42 extends between the primary end 26' of the cylinder 26 and the recess 29. Consequently, sterilizing gas can be introduced into the cavity formed by the recess 29 and thus subject all surfaces of this cavity to the sterilizing gas. The sterilizing groove of the small passage 43 is provided for symmetry reasons, see FIG. 5, i.e. during manufacturing the piston 28 may be introduced through either of the primary end 26' or the secondary end 26" of the cylinder 26. It should be noted that instead of providing the sterilizing grooves in the inner wall surface of the cylinder 26, corresponding grooves can be made in the outer surface of the piston 28.

The manufacturing of the medical product, including the container 3 and the connector 4, may be performed by filling the container with a medical fluid via an opening (not shown) that after filling is closed, e.g. by welding. In an alternative embodiment, the container is filled by a medical fluid via an opening that subsequently is closed by the connector 4. The medical product is then sterilized by means of an autoclaving process. During the autoclaving process, the medical product, e.g. including the connector 4 and the container 3, may be introduced in a closed space in a vessel. A sterilizing gas is introduced into the space of the vessel, and into the connector 4 via the small passages 41, 42, 43. The medical fluid in the container 3 is sterilized in a manner known per se, e.g. by means of heat generated in the space. The so sterilized medical fluid will ensure sterilization also of the interior of the second connection pipe 12. After the autoclaving process, the medical product is enclosed in an overwrap, that among other things ensures maintenance of the sterility of the product.

Figure 8:
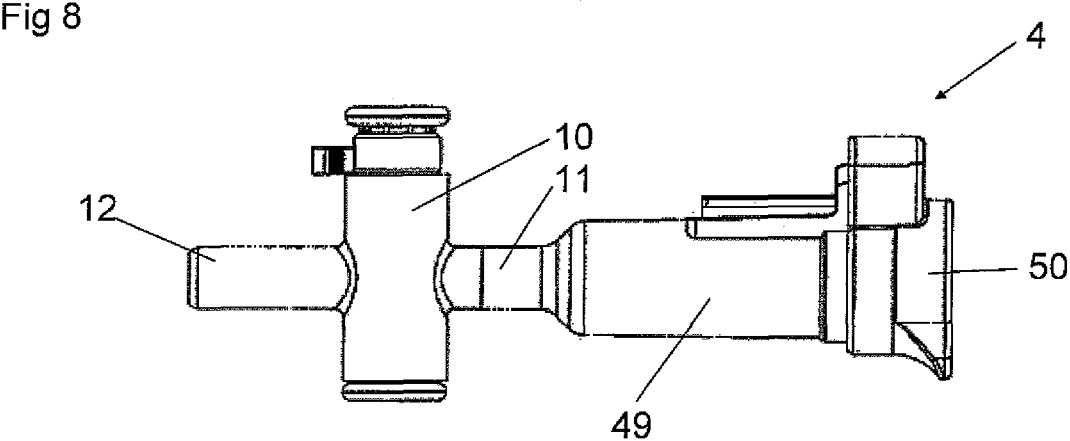
FIG. 8 discloses a side view of a connector of a medical product according to a second embodiment of the invention.

FIG. 8 discloses a second embodiment, which differs from the first embodiment in that the first connection pipe 11 has a different design with a different cover element 50. The first connection pipe 11 comprises a connecting element 49, which is known per se in the prior art. The cover element 50 in the form of a plug, which is known per se, is introduced into the first connecting pipe 11 and the connecting element 49. The plug is removed before use, e.g. before connector 4 is connected to a patient. The valve device 10 of the second embodiment is the same as the valve device 10 of the first embodiment.

FIGS. 9 to 14 disclose a third embodiment, wherein the valve device 10 comprises a first part 21 and a second part 22, which are rotatable in relation to each other with respect to an axis x' of rotation to permit an opening movement from a closed stable position, preventing fluid communication between the first connection pipe 11 and the second connection pipe 12, and an open stable position, see FIG. 14, forming a channel 73 permitting fluid communication between the first connection pipe 11 and the second connection pipe 12. The first connection pipe 11 is provided with a thread, see FIGS. 9 and 10, permitting the removable attachment of a cover element 35 of the kind described in conjunction with the description of the first embodiment. Also in the third embodiment, the first part 21 and the second part 22 are configured to remain in the open stable position when the open stable position has been obtained.

In the third embodiment, the first part 21 comprises a first abutment surface 61 through which the first connection pipe 11 extends via a first aperture 63. The second part 22 comprises a second abutment surface 62 through which the second connection pipe 12 extends via a second aperture 64. The first and second abutment surfaces 61, 62 are facing each other and are rotatable in relation to each other around the common axis x' of rotation. The first aperture 63 and the second aperture 64 are eccentric with respect to the axis x' of rotation. Consequently, the first connection pipe 11 and the second connection pipe 12 are at an angle distance from each other in the closed stable position but aligned to form the channel 73 extending straight through the connector 4 in the open stable position in parallel with the axis x' of rotation.

In the third embodiment disclosed, the first part 21 comprises a projecting member 65 and the second part 22 a projecting member 66. The projecting members 65 and 66 both have a wing-like shape and are configured to be engaged by a user as gripping members for performing the opening and closing movement of the valve device 10. As can be seen from FIGS. 9-12, in which the valve device 10 is in the closed stable position, the projecting members 65, 66 are at an angle distance from each other with respect to the axis x' of rotation.

In the open stable position, see FIG. 14, the projecting members 65, 66 are aligned seen in the direction of the axis x' of rotation.

In the third embodiment disclosed, the second part 22 comprises sealing means extending through the second abutment surface 62 around the second aperture 64. The sealing means comprises a groove 67 and a seal element 67a provided in the groove 67. It is to be noted that the sealing means could also be provided in the first part 21 to extend through the first abutment surface 61 around the first aperture 63.

In the third embodiment disclosed, a blocking member 68 is attached to the first part 21 to cooperate with the projecting member 66 of the second part 22 in such a way that the opening movement is prevented as long as the blocking member 68 is in the blocking state. Also in the third embodiment, the blocking member 68 is configured to permit the changing of the blocking state of the blocking member 68 to the non-blocking state by a user applying a determined force to the blocking member 68. The blocking member 68 is configured to permit the application of the force directly to the blocking member 68 itself. Moreover, the blocking member 68 is configured in such way that the changing of the blocking state of the blocking member 68 to the non-blocking state is performed, in an irreversible manner, by removing the blocking member 68 from the first part 21, wherein the blocking member 68 is attached to the first part 21 via a breakable attachment 69. In the non-blocking state, the first part 21 and the second part 22 are movable by a user applying a determined force in order to permit a closing movement from the open stable position, disclosed in FIG. 14, back to the closed stable position.

In the third embodiment, the first part 21 has a circumferential flange 70 extending around the first abutment surface 61 and forming a receiving cavity for the second part 22, see FIG. 12. The receiving cavity will determine the space in which the second part may be rotated. Furthermore, the relative rotation of the second part 22 and the first part 21 is controlled by a pin 71 protruding from the second abutment surface 62 into a curved groove 72 through the first abutment surface 61. The ends of the groove 72 determine the open stable position and the closed stable position, respectively.

In the third embodiment disclosed, the blocking member 68 is attached to the flange 70 of the first part 21. It is to be noted that the blocking member 68 of the third embodiment also could be attached at another position of the first part 21 or to the second part 22.

Also the connector 4 of the third embodiment comprises at least one small passage 41 through the cover element 35, see FIG. 13, permitting, in the closed stable position, an introduction of a sterilizing gas in such a way that the sterilizing gas will contact wall surfaces defining the channel 73. The small passage 41 enables sterilization of the connector 4 before use, i.e. before the blocking state of the blocking member 68 has been changed. Also in the third embodiment, the connector 4 could be sterilized together with the container 3 containing the medical fluid and the optional second connection portion 2a, for instance during an autoclaving process. The small passage 41 may extend through the cover element 35 as described in conjunction with the description of the first embodiment. Consequently, the inner wall surface of the first connection pipe 11 and a part of the second abutment surface 62 will thus be subjected to the sterilizing gas.

FIGS. 15 to 17 disclose a fourth embodiment according to which the first part 21 comprises a first pipe 91, and the second part 22 a second pipe 92. The first pipe 91 has an outer end portion forming the first connection pipe 11 and an inner end portion 93 having a closed end 94 but two opposite lateral opening 95, one of which is disclosed in FIG. 17. The first connection pipe 11 is of the same type as the first connection pipe 11 of the second embodiment, see FIG. 8, i.e. comprising a connecting element 49 and a cover element 50 in the form of a plug. The second pipe 92 forms the second connection pipe 12 and has an outer end portion 96. The second pipe 92 is configured to receive the first pipe 91 in an inner space of the second pipe 92. The second pipe 92 has connection means 97, known per se, for connecting the second pipe 92 to the secondary subsystem 2, and more specifically to the line of the secondary connection portion 2a. The second pipe 12 will then extend into the line of the secondary connection portion 2a, and be engaged to the secondary connection portion 2a by means of a thread 98 on the connecting means 97.

The first pipe 91 is movable along a longitudinal axis x" in the inner space of the second pipe 92 to permit the opening movement between the closed stable position, disclosed in FIGS. 15 to 17, and the open stable position. The first pipe 91 and the second pipe 92 are provided with a respective thread 101, 102 engaging each other. The opening movement along the longitudinal axis x" is obtained by rotating the first pipe 91 and the second pipe 92 relatively to each other. The first part 21, i.e. the first pipe 91, and the second part 22, i.e. the second pipe 92, are configured to remain in the open stable position when the open stable position has been obtained.

In the closed stable position, the lateral openings 95 are located opposite to an inner wall of the second pipe 92. In the open stable position, the inner end portion 93 and the lateral openings 95 of the first pipe 91 extend through and protrude from the outer end portion 96 of the second pipe 92. In the open stable position, a channel 103 is formed by an inner space of the first pipe 91. The lateral openings 95 will be introduced in the line of the secondary connection portion 2a, permitting fluid flow through the line of the secondary connection portion 2a into the channel 103 and further to the primary connection portion 1a and the primary subsystem 1.

In the fourth embodiment, the valve device 10 also comprises membrane 104 closing the channel 103 in the closed stable position. Breaking means 105 are provided and configured to break the membrane 104 during the opening movement in order to open the channel 103. As can be seen in FIG. 17, the membrane 104 is provided at, and closes, the outer end portion 96 of the second pipe 92, i.e. the membrane 104 cover the outer end portion 96. The breaking means 105 are formed by or at the inner end portion 93 of the first pipe 91. The breaking means 105, comprises in the fourth embodiment disclosed, a protrusion protruding from the inner end portion 93 of the first pipe 91.

Also in the fourth embodiment, a blocking member 108 is provided. The blocking member 108 is configured, in a blocking state, to prevent the opening movement from the closed stable position to the open stable position, and to permit, in an irreversible manner, changing of the blocking state of the blocking member 108 to a non-blocking state permitting the opening movement from the closed stable position to the open stable position. The blocking member 108 is provided on the first pipe 91. The blocking member 108 is attached to the first pipe 91 via a breakable attachment. The blocking member 108 is configured to permit the changing of the blocking state of the blocking member 108 to the non-blocking state by a user applying a determined force to the blocking member 108, directly to the blocking member 108 itself. In the fourth embodiment, the blocking member 108 may also be configured to permit the application of the force to at least one of the first part 21, i.e. the first pipe 91, and the second part 22, i.e. the second pipe 92. Moreover, the blocking member 108 is configured in such way that the changing of the blocking state of the blocking member 108 to the non-blocking state is performed by removing the blocking member 108 from the first pipe 91. In the non-blocking state, the first part 21, i.e. the first pipe 91, and the second part 22, i.e. the second pipe 92, are movable by a user applying a determined force in order to permit a closing movement from the open stable position to the closed stable position.

It is to be noted, that the first connection pipe 11, as an alternative, may be configured as the first connection pipe in the first and third embodiments, i.e. adapted to receive the cover element 35.

Figure 18:
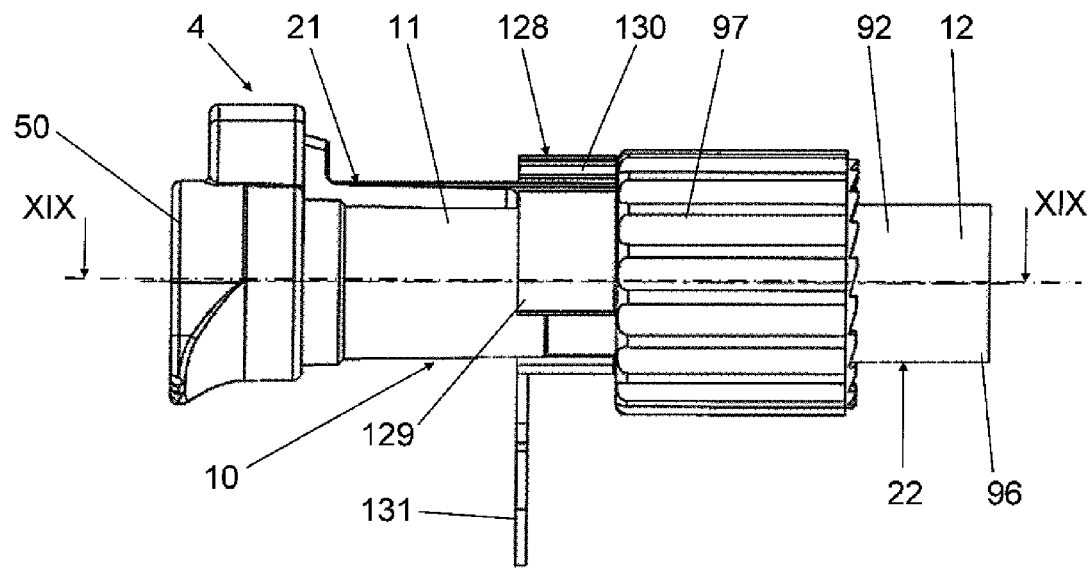
FIG. 18 discloses a side view of a connector of a medical product according to a fifth embodiment of the invention.
Figure 19:
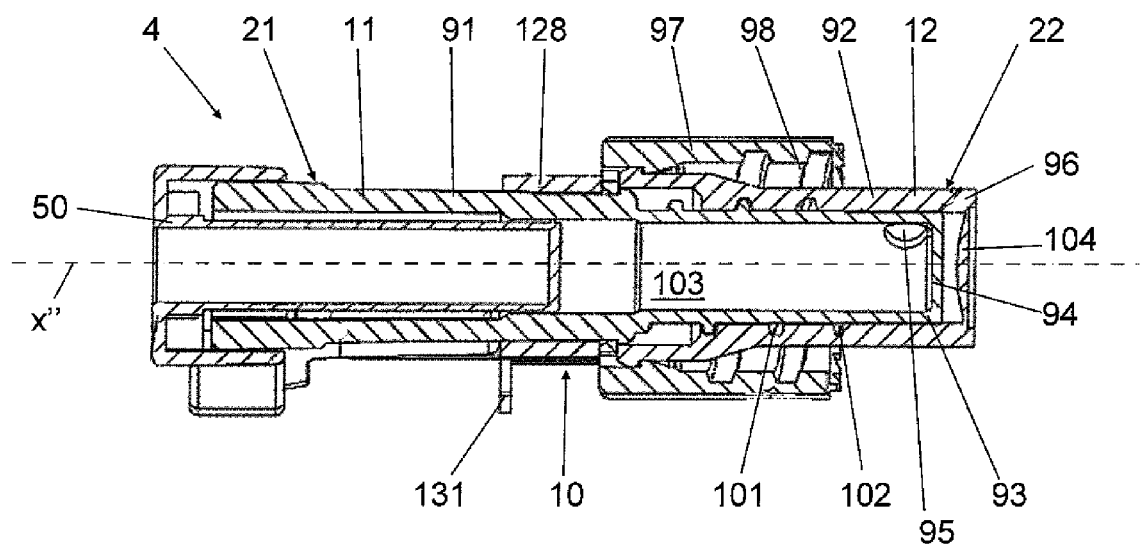
FIG. 19 discloses a sectional view along the lines XIX-XIX in FIG. 18.

FIGS. 18 and 19 disclose a fifth embodiment which differs from the fourth embodiment with respect to the design and mounting of the blocking member. In the fifth embodiment, a blocking member 128 is provided. The blocking member 128 comprises a removable ring 129 extending around the first pipe 91, and more precisely around a main part of the periphery of the first pipe 91. The ring 129 has a gripping member 130 extending outwardly to be gripped by the user for removing the ring from the first pipe 91. The ring 129 is also connected to the cover element 50, i.e. the plug, via a connection strip 131.

A further difference over the fourth embodiment, is that the inner end portion 93 has no protrusion, but the breaking means is formed by the inner end portion 93 as such.

The invention is not limited to the embodiments disclosed but may be varied and modified within the scope of the following claims.

The invention claimed is:

1. A medical product configured for use in a medical system comprising:

a first subsystem having a first connection portion and a second subsystem having a second connection portion, at least one of the first and second subsystems containing a medical fluid, the medical product comprising a connector configured to connect the first and second subsystems to each other to permit transport of the medical fluid from one of the first and second subsystems to the other of said first and second subsystems, the connector comprising:
  a valve device;
  a first connection pipe connected to the valve device and configured to be connected to the first connection portion of the first subsystem; and
  a second connection pipe connected to the valve device and configured to be connected to the second connection portion of the second subsystem;

the valve device comprising a first part and a second part, said first and second parts being movable in relation to each other to permit an opening movement from a closed stable position, said closed stable position preventing fluid communication between the first connection pipe and the second connection pipe, to an open stable position, said opening movement to the open stable position forming a channel permitting fluid communication between the first connection pipe and the second connection pipe, wherein the medical product comprises a blocking member configured, in a blocking state, to prevent the opening movement from the closed stable position to the open stable position, said blocking member being further configured to permit changing of the blocking state of the blocking member to a non-blocking state permitting the opening movement from the closed stable position to the open stable position, wherein the first part and the second part are configured to remain, without application of an external force, in the open stable position after the open stable position has been obtained.

2. A medical product according to claim 1, wherein the blocking member is provided on the valve device.

3. A medical product according to claim 1, wherein the blocking member is configured to permit the changing of the blocking state of the blocking member to the non-blocking state by a user applying a determined force to the blocking member.

4. A medical product according to claim 3, wherein the blocking member is configured to permit the application of the determined force directly to the blocking member itself.

5. A medical product according to claim 3, wherein the blocking member is configured to permit the application of the determined force to at least one of the first part and the second part.

6. A medical product according to claim 1, wherein the blocking member is configured to permit the changing of the blocking state of the blocking member to the non-blocking state is to be performed by removing the blocking member.

7. A medical product according to claim 1, wherein the first part and the second part, in the non-blocking state of the blocking member, are movable by a user applying a determined force in order to permit a closing movement from the open stable position to the closed stable position.

8. A medical product according to claim 1, wherein the medical product comprises a cover element configured to be attached to the first connection pipe for protecting the interior of the first connection pipe, wherein the cover element is removable before the first connection pipe is connected to the first connection portion of the first subsystem.

9. A medical product according to claim 1, wherein the second subsystem comprises a container containing the medical fluid, said container comprising the medical product and being connected to the second connection pipe of the connector.

10. A medical product according to claim 1, wherein the blocking member is configured to permit changing of the blocking state to the non-blocking state in an irreversible manner by a breakable attachment.

11. A medical product according to claim 1, wherein the first part comprises a housing through which the channel extends, said housing comprising cylinder forming an inner chamber extending transversally to and crossing the channel, and wherein the second part comprises a piston, is said piston being movable in the inner chamber between the closed stable position closing the channel and the open stable position in which the channel is open by a recess in the piston.

12. A medical product according to claim 11, wherein the blocking member is provided on one of the piston and the cylinder.

13. A medical product according to claim 12, wherein the cylinder has a primary end and a secondary end and the piston has a primary end and a secondary end, wherein the primary end of the piston protrudes from the primary end of the cylinder in the closed stable position and where-in the secondary end of the piston protrudes from the secondary end of the cylinder in the open stable position.

14. A medical product according to claim 13, wherein the blocking member is provided on the piston at the primary end of the piston.

15. A medical product according to claim 14, wherein the blocking member is configured as a part of a removable ring extending around the piston at the primary end.

16. A medical product according to claim 13, wherein the piston has a primary end portion provided at the primary end of the piston, said primary end portion of the piston being configured to prevent the primary end of the piston from entering the inner chamber of the cylinder, and a secondary end portion provided at the secondary end of the piston, said secondary end portion of the piston being configured to prevent the secondary end of the piston from entering the inner chamber of the cylinder.

17. A medical product according to claim 15, wherein the removable ring is provided between the primary end of the cylinder and the primary end portion of the piston.

18. A medical product according to claim 15, wherein the blocking member is attached to the piston via a breakable attachment.

19. A medical product according to claim 11, wherein the piston is made of a piston material and the cylinder is made of a cylinder material, wherein the piston material is softer than the cylinder material.

20. A medical product according to claim 11, wherein the piston is provided with a seal abutting against an inner wall of the cylinder.

21. A medical product according to claim 20, wherein the seal comprises at least one ridge extending outwardly from an outer surface of the piston and around an outer periphery of the piston.

22. A medical product according to claim 1, wherein the first part comprises a first abutment surface through which the first connection pipe extends via a first aperture and the second part comprises a second abutment surface through which the second connection pipe extends via a second aperture, wherein the first and second abutment surfaces are configured to face each other and are rotatable in relation to each other around a common axis of rotation, said first aperture and said second aperture are being eccentric with respect to the axis of rotation.

23. A medical product according to claim 22, wherein one of the first part and the second part comprises a projecting member, and wherein the blocking member is attached to the other of said first and second parts not comprising the projecting member, said blocking member being configured to cooperate with the projecting member to prevent the opening movement as long as the blocking member is in the blocking state.

24. A medical product according to claim 23, wherein the first part comprises a first projecting member and the second part comprises a second projecting member, wherein the first and second projecting members are aligned in the open stable position and at an angle distance from each other with respect to the axis of rotation in the closed stable position.

25. A medical product according to claim 22, wherein one of the first part and the second part has a circumferential flange extending around the first abutment surface or the second abutment surface, thereby forming a receiving cavity for the other of the first part and the second part not comprising the circumferential flange.

26. A medical product according to claim 22, wherein at least one of the first part and the second part comprises a seal extending through the first abutment surface or the second abutment surface around the first aperture or the second aperture.

27. A medical product according to claim 26, wherein the seal comprises a groove and a seal element provided in the groove.

28. A medical product according to claim 1, wherein the valve device comprises a membrane closing the channel in the closed stable position, and a breaking device configured to break the membrane during the opening movement in order to open the channel.

29. A medical product according to claim 1, wherein the first part comprises a first pipe, said first pipe having an outer end portion forming the first connection pipe and an inner end portion having a closed end but at least one lateral opening, and wherein the second part comprises a second pipe, said second pipe forming the second connection pipe and being configured to receive the first pipe, said first pipe being movable along a longitudinal axis in the second pipe to permit the opening movement between the closed stable position, in which the lateral opening is located opposite to an inner wall of the second pipe, and the open stable position, in which the inner end portion and the lateral opening of the first pipe protrude from outer end portion of the second pipe.

30. A medical product according to claim 28, wherein the membrane is provided at the second pipe to cover the outer end portion, and wherein the breaking device is formed by the inner end portion of the first pipe.

31. A medical product according to claim 30, wherein the breaking device comprises a protrusion protruding from the inner end portion of the first pipe.

32. A medical product according to claim 29, wherein the first pipe and the second pipe are provided with at least one thread and wherein the opening movement along the longitudinal axis is obtained by rotating the first and second pipes relative to each other.

33. A medical product according to claim 28, wherein the blocking member is provided on the first pipe.

34. A medical product according to claim 33, wherein the blocking member is attached to the first pipe via a breakable attachment.

35. A medical product according to claim 33, wherein the blocking member comprises a removable ring extending around a main part of the first pipe.

36. A medical product configured for use in a medical system comprising:
a first subsystem having a first connection portion,
the medical product comprising a container containing a medical fluid and a connector configured to connect the first subsystem to the container to permit transport of the medical fluid from the container to the first subsystem,
the connector comprising:
a valve device;
a first connection pipe connected to the valve device and configured to be connected to the first connection portion of the first subsystem; and
a second connection pipe connected to the valve device and to the container,
the valve device comprising a first part and a second part, said first and second parts being movable in relation to each other to permit an opening movement from a closed stable position, said closed stable position preventing fluid communication between the first connection pipe and the second connection pipe, and an open stable position, said open stable position forming a channel permitting fluid communication between the first connection pipe and the second connection pipe, wherein the first part and the second part are configured to remain in the open stable position, without application of an external force, after the open stable position has been obtained,
wherein the medical product comprises a blocking member configured, in a blocking state, to prevent the opening movement from the closed stable position to the open stable position, said blocking member being further configured to permit changing of the blocking state of the blocking member to a non-blocking state permitting the opening movement from the closed stable position to the open stable position.

37. A method of handling a medical system comprising a first subsystem having a first connection portion and a second subsystem having a second connection portion, at least one of the first and second subsystems containing a medical fluid, by a connector connecting the first and second subsystems to each other, said connector comprising a valve device comprising a first part and a second part; a first connection pipe connected to the valve device and configured to be connected to the first connection portion of the first subsystem; and a second connection pipe connected to the valve device and configured to be connected to the second connection portion of the second subsystem, the method comprising:
changing a blocking state of a blocking member, said blocking state preventing an opening movement of the first part and the second part in relation to each other, to a non-blocking state;
applying a force to move the first part and the second part in relation to each other from a closed stable position, said closed stable position preventing fluid communication between the first connection pipe and the second connection pipe, and an open stable position, said open stable position forming a channel permitting fluid communication between the first connection pipe and the second connection pipe;
after releasing the force that moved the first part and second part in relation to each other, maintaining, without application of an external force, the open stable position of the first part and the second part, and while the valve is in the open stable position, transporting the medical fluid from one of the first and second subsystems to the other of said first and second subsystem.

* * * * *

UNITED STATES PATENT AND TRADEMARK OFFICE
CERTIFICATE OF CORRECTION

PATENT NO. : 8,469,931 B2  Page 1 of 1
APPLICATION NO. : 12/531023
DATED : June 25, 2013
INVENTOR(S) : Tryggvason et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 642 days.

Signed and Sealed this
Eighth Day of September, 2015

Michelle K. Lee
*Director of the United States Patent and Trademark Office*